United States Patent
Shuster et al.

(10) Patent No.: US 6,242,456 B1
(45) Date of Patent: Jun. 5, 2001

(54) TREATMENT OF STEREOTYPIC, SELF-INJURIOUS AND COMPULSIVE BEHAVIORS IN MAN AND ANIMALS USING ANTAGONISTS OF NMDA RECEPTORS

(75) Inventors: Louis Shuster, Brighton; Nicholas H. Dodman, Grafton, both of MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 09/262,546

(22) Filed: Mar. 4, 1999

Related U.S. Application Data

(60) Provisional application No. 60/077,312, filed on Mar. 9, 1998.

(51) Int. Cl.$^7$ ............................................... A61K 31/44
(52) U.S. Cl. ............................................... 514/282
(58) Field of Search ............................................... 514/282

(56) References Cited

U.S. PATENT DOCUMENTS

| | | | |
|---|---|---|---|
| 4,692,451 | 9/1987 | Dodman et al. | 514/282 |
| 5,519,032 | 5/1996 | Effland et al. | 514/301 |
| 5,654,281 | 8/1997 | Mayer et al. | 514/25 |
| 5,849,762 | 12/1998 | Farrar et al. | 514/327 |

FOREIGN PATENT DOCUMENTS

| | | |
|---|---|---|
| WO 91/19493 | 12/1991 | (WO) . |
| WO 97/23202 | 7/1997 | (WO) . |
| WO 97/33581 | 9/1997 | (WO) . |
| WO 98/03189 | 1/1998 | (WO) . |

OTHER PUBLICATIONS

Koyuncuoğlu, H. et al., "The treatment of heroin addicts with dextromethorphan: A double–blind comparison of dextromethorphan with chlorprozamine," *Int. J. Clin. Pharmacol. Ther. Toxicol.*, 28(4):147–152 (1990).

Welch, L. et al., "The treatment of a chronic organic mental disorder with dextromethorphan in a man with severe mental retardation," *Br. J. Psychiatry*, 161:118–120 (1992).

Pomerleau, O.F., "Endogenous opioids and smoking: A review of progress and problems," *Psychoneuroendocrinology*, 23(2):115–130 (1998).

Smith, K.C. et al., "Naltrexone for neurotic excoriations," *J. Am. Acad. Dermatol.*, 20(5):860–861 (1989).

Dodman, N.H. et al., "Use of narcotic antagonists to modify stereotypic self–licking, self–chewing, and scratching behavior in dogs," *JAVMA*, 193(7):815–819 (1988).

Aabech, H.S., "Tourette syndrome: New aspects on pharmacological treatment," *Tidsskr. Nor. Laegeforen.*, 109(9):961–963 (1989).

Dodman, N.H. et al., "Investigation into the use of narcotic antagonists in the treatment of a stereotypic behavior pattern (crib–biting) in the horse," *Am. J. Vet. Res.*, 48(2):311–319 (1987).

Crockford, D.N. et al., "Naltrexone in the treatment of pathological gambling and alcohol dependence," *Can. J. Psychiatry*, 43(1):86 (1998).

Keuthen, N.J. et al., "Trichotillomania, Current issues in conceptualization and treatment," *Psychother. Psychosom.*, 67(4–5):202–213 (1998).

Mills, I.H. et al., "Treatment of compulsive behaviour in eating disorders with intermittent ketamine infusions," *Q.J.Med.*, 91(7):493–503 (1998).

Herling, S. et al., "Discriminative stimulus effects of dextrorphan in pigeons," *J. Pharmacol. Exp. Ther.*, 227(3):723–731 (1983) Abstract.

Woods–Kettelberger, A. et al., "Animal models with potential applications for screening compounds for the treatment of obsessive–compulsive disorders," *Exp. Opin. Invest. Drugs*, 6(10):1369–1381 (1997).

Ghaziuddin, M. et al., "Haloperidol treatment of trichotillomania in a boy with autism and mental retardation," *J. Autism and Developmental Disorders*, 21(3):365–371 (1991).

Pulvirenti, L. et al., "Dextromethorphan reduces intravenous cocaine self–administration in the rat," *Eur. J. Pharmacol.*, 321:279–283 (1997).

Choi, D.W. and Viseskul, V., "Opioids and non–opioid enantiomers selectively attenuate N–methyl–D–aspartate neurotoxicity on cortical neurons," *Eur. J. Pharmacol.*, 155:27–35 (1988).

Lipton, S.A. and Rosenberg, P.A., "Excitatory Amino Acids as a Final Common Pathway for Neurologic Disorders," *N. Engl. J. Med.*, 330(9):613–622 (1994).

O'Connor, P.G. et al., "A Preliminary Investigation of the Management of Alcohol Dependence with Naltrexone by Primary Care Providers," *Am. J. Med.*, 103(6):477–482 (1997).

Overall, K.L., "Recognition, Diagnosis, and Management of Obsessive–Compulsive Disorders," *Canine Practice*, 17(4):39–43 (1992).

Chatterjie, N. et al., "Dextro–Naloxone Counteracts Amphetamine–Induced Hyperactivity," *Pharmacol. Biochem. Behav.*, 59(2):271–274 (1998).

Dodman, N.H. and Olivier, B., "In Search of Animal Models for Obsessive–Compulsive Disorder," *CNS*, Nov. 1996.

(List continued on next page.)

Primary Examiner—Kevin E. Weddington
(74) Attorney, Agent, or Firm—Hamilton, Brook, Smith, Reynolds, P.C.

(57) ABSTRACT

NMDA receptor antagonists can be used in methods of treatment, for reducing the frequency of stereotypic behaviors in animals and for reducing the frequency of analogous compulsive behaviors in humans, for example, those that have been said to be a manifestation of, or related to, obsessive-compulsive disorder. Of particular interest are the (+) enantiomers of opioid receptor binding compounds, which can reduce the frequency of the behaviors, while having no effects from binding at the opioid receptor.

12 Claims, 4 Drawing Sheets-

OTHER PUBLICATIONS

White, S.D., "Naltrexone for treatment of acral lick dermatitis in dogs," *JAVMA*, 196(7):1073–1076 (1990).

Ebert, B. et al., "Opioid Analgesics as Noncompetitive N–Methyl–D–aspartate (NMDA) Antagonists," *Biochem. Pharmacol.*, 56:553–559 (1998).

Gorman, A.L. et al., "The d–and l–isomers of methadone bind to the non–competitive site on the N–methyl–D–aspartate (NMDA) receptor in the rat forebrain and spinal cord," *Neurosci. Lett.*, 223:5–8 (1997).

International Search Report for PCT/US99/04680; International Filing Date Mar. 4, 1999; Earliest Filing Date Mar. 9, 1998.

TREATMENT OF STEREOTYPIC, SELF-INJURIOUS AND COMPULSIVE BEHAVIORS IN MAN AND ANIMALS USING ANTAGONISTS OF NMDA RECEPTORS

RELATED APPLICATION

This application claims the benefit of U.S. Provisional Application No. 60/077,312 filed on Mar. 9, 1998, the entire teachings of which are incorporated herein by reference.

BACKGROUND OF THE INVENTION

Stereotypic behavior in animals (also called "repetitive" or "compulsive" behavior) has been defined by some researchers as acts that are repetitive and constant, which may appear to serve no obvious purpose, and may even be injurious. One of the most common of these behaviors is, for example, crib-biting by horses—grabbing and biting of the feed bin or of parts of the structure in which the horse is housed (also called "cribbing"—see U.S. Pat. No. 4,692,451 for a description of this behavior, associated behaviors, and resulting problems). Another common behavior in dogs is compulsive licking of itself—even to the point of aggravating a sore ("lick granuloma" or "acral lick"). Stereotypies may show some degree of variation, and may be unlike the more typical behaviors such as cribbing and licking, in that they have no features of repetitive motion, but are characterized rather by motionless staring or a frozen body position.

The repetitive behaviors of animals and the compulsive behaviors of humans have both responded to treatment with some of the same drugs. See, e.g., regarding treatment of acral lick with drugs that have shown benefit in human obsessive-compulsive disorder (OCD), Rapoport, J. L., *Clin. Neurophar.* 15:Suppl. 1 Pt A:261A–262A, 1992; Rapoport, J. L. et al., *Arch. Gen. Psychiatry* 49:517–521, 1992. See also Smith, K. C. and Pittlekow, M. R., *J. Am. Dermatol.* 20:860–861, 1989, wherein it was reported that onychophagia and skin picking responded to treatment with (−) enantiomers of opioid antagonists, which have been effective also in compulsive hair pulling in cats, feather picking in birds, acral lick in dogs and cribbing in horses (Dodman, N. H., *Vet. International* 6:13–20, 1994; Dodman, N. H. et al., *J. Am. Vet. Med. Assoc.* 193:815–819, 1988; Turner, R., Proceedings of Annual Conference of the Association of Avian Veterinarians: Aug. 31–Sept. 4, 1993, Nashville, Tenn., pp. 116–118). See also U.S. Pat. No. 4,692,451, the contents of which are incorporated herein by reference in their entirety. Studies of this type provide justification for the conclusion that the same underlying physiological processes are involved in causation of the animal and human behaviors. Therefore, they should all respond positively to new methods of therapy.

SUMMARY OF THE INVENTION

The invention relates to a method for treating a disorder in animals, variously termed repetitive, stereotypic, or compulsive behavior, and which can also be self-injurious, by administering to the animal, by one or more appropriate routes and by appropriate doses, an effective amount of one or more NMDA receptor antagonists. In some cases, the composition comprises one or more NMDA receptor antagonists that are not haloperidol. In some cases the composition comprises one or more NMDA receptor antagonists, and does not comprise an opioid receptor agonist or antagonist which is primarily (−) enantiomer. In some cases the composition comprises one or more NMDA receptor antagonists, but does not comprise an opioid receptor agonist or antagonist of either (+) or (−) enantiomer.

The invention, more particularly, is a method for treating compulsive behaviors in horses, such as crib biting, wind sucking, stall walking, weaving, head bobbing, pawing, tonguing, self-biting, flank sucking, and head shaking, by administering to the horse a composition comprising one or more NMDA receptor antagonists.

In another particular embodiment, the invention is a method for treating compulsive behaviors in dogs, such as compulsive licking (acral lick), tail chasing and whirling, pacing, fly chasing, shadow or light chasing, excessive barking, stone eating, excessive drinking, and excessive eating, comprising administering to the dog an effective amount of an NMDA receptor antagonist.

Also an embodiment of the invention is a method for treating compulsive behaviors in cats, such as wool sucking, compulsive licking, tail chasing, hoarding, pacing, excessive marking, compulsive masturbation, and compulsive aggression.

A further embodiment of the invention is a method for treating compulsive behaviors in birds, such as feather and skin picking.

The invention relates to a method for treating a disorder (or more than one disorder, as it is possible that two or more can occur together) in humans, variously termed repetitive, stereotypic, or compulsive behavior, and which can also be self-injurious, by administering to the human, by one or more appropriate routes and by appropriate doses, one or more NMDA receptor antagonists, thereby relieving the frequency and/or intensity of the compulsion and reducing the frequency and/or intensity of the behavior.

Examples of the human behaviors which can be treated by these methods include, but are not limited to: obsessive-compulsive disorder (with its various manifestations of checking, counting, washing to remove contamination, etc.), trichotillomania, psychogenic excoriation, nail biting, compulsive exercising, smoking compulsion, drug (opioid) addiction, and alcohol addiction. These compulsive behaviors may be related also to compulsive gambling, compulsive shopping, and eating disorders.

DETAILED DESCRIPTION OF THE INVENTION

Figure 1:
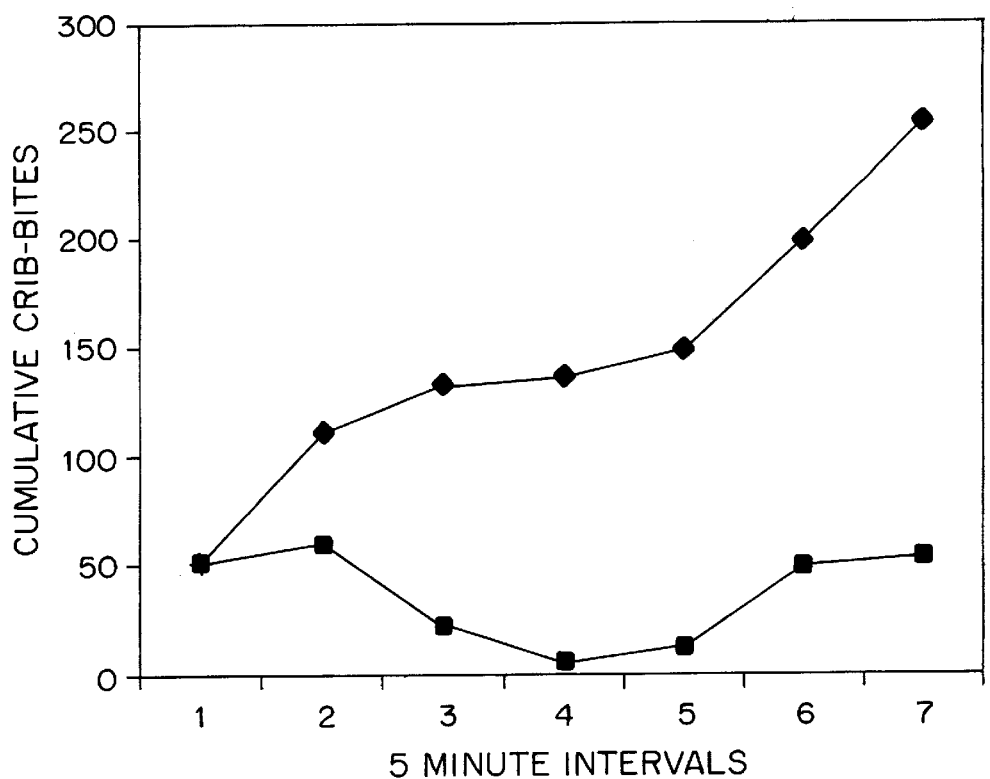
FIG. 1 is a graph in which cumulative crib-bites per time after administration of D-methadone (diamonds), as well as the rate of crib-bites per 5-minute interval (squares) are plotted, showing the effect of D-methadone on the rate of compulsive crib-biting in horses.

The invention relates to methods of treating animals displaying various types of repetitive and/or compulsive (frequently also called stereotypic) behaviors using compounds that are characterizable as NMDA receptor antagonists (having specific binding activity to NMDA receptors and/or the ability to block activation of the NMDA ligand-gated channel by an activating compound).

Compulsive or stereotypic behaviors in dogs can be put into several categories. "Grooming behaviors" can include, for example, lick granuloma (acral lick), compulsively licking objects, self-scratching, chewing feet, hair and nails, etc., flank sucking and air licking. "Locomotory behaviors" can include, for example, running and jumping, pacing, head shaking, paw shaking, tail swishing, freezing, whirling, tail chasing, walking in a pattern, as along a fence, digging and floor scratching. "Vocalization behaviors" include, for example, rhythmic barking, growling or snarling at self, barking at food, crying and howling. "Predatory behaviors" include, for instance, staring, air batting, jaw snapping, pouncing, prey chasing or searching, ducking, and fly chasing. "Eating and drinking behaviors" include, for example, excessive drinking, polyphagia, excessive drooling, gravel and dirt eating, stone chewing, wool sucking, and eating fabrics. "Sexual behaviors" include, for example, compulsive mounting. See, for tables compiling the observed behaviors of not only cats and dogs, but also horses, primates and other species Dodman, N. H., "Veterinary Models of Obsessive-Compulsive Disorder," Chapter 16, pp. 319–334 In *Obsessive-Compulsive Disorders: Practical Management* (M. A. Jenike et al., eds.), Moseby, Boston, 1998. See also N. H. Dodman et al., "Veterinary Models of OCD," Chapter 6, pp. 99–143, In *Obsessive-Compulsive Disorders. Diagnosis, Etiology and Treatment,* (E. Hollander et al., eds.), Marcel Dekker, New York, 1997. See also Tables 1 and 2 in Luescher, U. A. et al., "Stereotypic or Obsessive-Compulsive Disorders in Dogs and Cats," In *Veterinary Clinics of North America: Small Animal Practice* 21(2):401–413 (March, 1991).

Cats can exhibit behaviors similar to those seen in dogs, with the most common behaviors being those related to grooming, such as excessive self-licking and hair chewing. Other repetitive behaviors are tail chasing, hoarding, wool sucking, pacing, excessive marking, compulsive masturbation, and compulsive aggression.

Horses have not been observed to display compulsive predatory behaviors, but can also suffer from species-typical compulsive behaviors, such as cribbing, wind sucking, stall walking, weaving, head bobbing, pawing, lip flapping/ tonguing, head shaking, flank biting, trichotillomania, and masturbation.

Birds, especially those of the order Psittaci, which includes parakeets, cockatoos, lories, macaws, and South American and African parrots, are subject to compulsive behaviors, particularly feather pulling and skin picking, but also route tracing, spot picking, masturbation and regurgitation.

Compulsive behaviors exhibited by animals of the porcine species include bar biting, vacuum chewing, and chain chewing.

Animals of the ovine and bovine species can exhibit behaviors similar to those seen in other species. These include tonguing and compulsive sucking, weaving, hair licking, and masturbation.

Bears in captivity have developed pacing behaviors.

Primates in captivity have been observed to have the following compulsive behaviors: hair pulling and skin picking (categorized as "grooming" behaviors), self sucking, licking and chewing ("consummatory" behaviors), self-directed aggression ("aggressive" behavior), masturbation and rectal probing (sexual behaviors), and bouncing in place and somersaulting (locomotory behaviors).

Humans, as would be expected, have developed a great variety of compulsive behaviors, compared to those of the animals. Common human behaviors include: paraphilias (sexual); self-directed aggression and pyromania (aggressive); checking, avoidance of contamination (fear and avoidance); skin/nose picking, trichotillomania (grooming); gambling, hoarding ("predatory"); whirling, tics, compulsive exercising (locomotor); and binge eating (consummatory). This list, like the lists of behaviors of the animals given above, is not intended to be complete or limiting, as variations with each individual animal or human are possible. Further descriptions of human compulsive behaviors can be found in *Diagnostic and Statistical Manual of Mental Disorders* (DSM-IV™), American Psychiatric Association, 1994.

Stereotypic animal behaviors have been compared to obsessive-compulsive disorder and disorders involving similar repetitive or compulsive behaviors in humans. As Freud described compulsive behavior, "the patient is impelled to perform actions which not only afford him no pleasure but from which he is powerless to desist." It has been hypothesized that a more satisfactory definition of stereotypies or compulsive behaviors would encompass both the animal and human syndromes, by being based on common, specific neuropathologic differences in the brains of animals or humans manifesting these behaviors, compared to animals or humans that do not manifest such behaviors. See discussion in Luescher, U. A. et al., "Stereotypic or Obsessive-Compulsive Disorders in Dogs and Cats," In *Veterinary Clinics of North America: Small Animal Practice* 21(2):401–413 (March 1991).

The similarities have led some to refer to not only the human behaviors, but also the animal behaviors, as "compulsive" behaviors or "obsessive-compulsive disorders." See Overall, K. L., *Canine Practice* 17:39–42, 1992; Dodman, N. H. and B. Olivier, *CNS Spectrums* 1(2):10–15, 1996. It has been proposed that acral lick in dogs, and compulsive bar biting and chain chewing of tethered sows, as well as several other behaviors of animals, might serve as useful models of human obsessive-compulsive disorder (Dodman, N. H. and B. Olivier, *CNS Spectrums* 1(2):10–15, 1996). Compulsive self-grooming behaviors in animals, in particular, have been compared with trichotillomania in humans (Moon-Fanelli, A. A. et al., Chapter 3, pp. 63–92 In *Trichotillomania,* (D. J. Stein et al., eds.), American Psychiatric Press, Inc., Washington, D.C. The serotonin reuptake inhibitor citalopram has been found to be useful in the treatment of OCD and possibly compulsive hair-pulling in humans, and has been used successfully in the majority of the dogs in the study reported, to treat acral lick dermatitis (Stein, D. J. et al., *Depression and Anxiety* 8:39–42, 1998). These data provide evidence that acral lick dermatitis can be a useful animal analog of OCD.

Similarities that can be observed among the repetitive animal behaviors, and between the repetitive behaviors of animals and the repetitive behaviors of humans, suggest a common etiology. In addition, there are studies that link one human syndrome to another. Neurologic disorders such as epilepsy, Sydenham's chorea, and toxic and vascular lesions of the basal ganglia have been found concurrently with OCD (Freeman, J. et al., *Paediatrics* 35:42–49, 1965; Kettle, P. and I. Marks, *Br. J. Psychiatry* 149:315–319, 1989), leading to the suggestion that repetitive behaviors may be a sign of acquired disease. Observation of increased rates of OCD in Tourette syndrome (TS) patients, increased prevalence of tics and TS in OCD patients, and the increased familial rates of OCD and TS in first-degree relatives of both TS and OCD probands lead to the conclusion that there is a genetic association between the two disorders (Leonard, H. L., et al., *Am. J. Psych.* 149:1244–1251, 1992; Leonard, H. L., et al., *Adv. Neurol.* 58:83–93, 1992). A study of the incidence of OCD in the first degree relatives of trichotillomania patients found a higher lifetime prevalence of OCD in this group than in the relatives of normal controls (Lenane, M. C. et al., *J. Child Pyschol. Psychiatry* 33(5):925–933, 1992). Attention deficit/hyperactivity disorder occurs frequently with Tourette syndrome (see, for example, Harris, E. L. et al., *J. Int. Neuropsychol. Soc.* 1(6):511–516, 1995).

N-methyl-D-aspartic acid (NMDA) selectively activates a major subclass of glutamatergic excitatory amino acid receptors in the vertebrate central nervous system (CNS). The NMDA receptor is a ligand-gated channel that is activated by the coagonists glutamate (or selectively in vitro by NMDA) and glycine acting at a strychnine-insensitive glycine site (Wong, E. H. F. and J. A. Kemp, *Annu. Rev. Pharmacol. Toxicol* 31:401–425, 1991). It is further subject to regulation by a voltage-dependent block of the channel by $Mg^{2+}$, a voltage-independent action of $Zn^{2+}$, the redox state of the receptor, arachidonic acid, ethanol, neurosteroids, pH and polyamines.

Although the exact structure of NMDA receptors is still a matter of debate, NMDA-sensitive ionotropic glutamate receptors probably consist of tetrameric, heteromeric, subunit assemblies that have different physiological and pharmacological properties and are differentially distributed throughout the central nervous system. The NMDA receptors are positively modulated by glycine, by polyamines (spermine and spermidine), by histamine and, under some conditions, by cations. NMDA receptors are coupled to glutamate-gated high conductance channels permeable to $K^+$, $Na^+$, and $Ca^{++}$, that are critical for long-term potentiation, and are selectively activated by the artificial glutamate analog N-methyl-D-aspartate. There is evidence that NMDA receptors play an important role in learning and in other phenomena in the brain, such as drug dependence and addiction, chronic pain, and CNS development, as well as in normal or disturbed synaptic transmission in some areas of the CNS. See, for review on NMDA receptors, Danysz, W. and Parsons, C. G., *Pharmacological Reviews* 50(4):597–664, 1998.

An NMDA receptor antagonist is any one of a number of agents which has been shown to bind to NMDA receptors and/or block any of the sites that bind glycine, glutamate, NMDA or phencyclidine (PCP). Blocking the NMDA receptor sites has the effect of preventing the creation of an action potential in the cell. NMDA receptor antagonists include those compounds that preferentially bind to NMDA receptors, but may also have other activities.

NMDA receptor antagonists include the following: previously identified competitive and non-competitive antagonists of NMDA receptors, which may bind, for instance, at the glycine site (on the NR1 subunit) and/or at the glutamate recognition site (on the NR2 subunit). Preferred NMDA receptor antagonists are those that have the ability to cross the blood-brain barrier and also demonstrate a low incidence of side effects. Such NMDA receptor antagonists can include, for example, compounds known as arylcyclohexylamines such as the anesthetic ketamine, neuroleptics such as haloperidol (Coughenour, L. L. and J. J. Corden, *J. Pharmacol. Exp. Ther.* 280:584–592, 1997) and the anti-Parkinson drug amantadine. Ifenprodil and eliprodil are neuroprotective agents whose mechanism of action has been attributed to their NMDA antagonist properties (Scatton, B. et al., pp. 139–154 In Direct and Allosteric Control of Glutamate Receptors, Palfreyman, M. G. et al., eds., CRC Press, 1994). Trifluperidol and haloperidol have been shown to have a similar selectivity for the NR1a/NR2B receptor subtype expressed in Xenopus oocytes (Ilyin, V. et al., *Soc. Neurosci. Abstracts* 21:835, 1995. Memantine, felbamate, ifenprodil, eliprodil, CGS19755, remacemide, and CNS 1102 are also antagonists of NMDA receptors (Lipton, S. A. and P. A. Rosenberg, *New England Journal of Medicine* 330 (9):613–622, 1994). A large number of NMDA receptor antagonists have been synthesized and tested for interaction with the NMDA receptor complex, and research into the synthesis and improvement of NMDA receptor antagonists is continuing. See, for example, U.S. Pat. No. 5,783,700, WO 97/10240, U.S. Pat. No. 5,710,168, WO 98/03189, and DE 19601782.

NMDA receptor antagonists also include newer preparations under development e.g., CP 101, 606 (Di, X. et al., *Stroke* 28:2244–2251, 1997) BIII CL (Grauert, M. et al., *J. Pharmacol. Exp. Ther.* 285:767–776, 1998); AR-R15896AR (Palmer, C. G. et al., *J. Pharmacol. Exp. Ther.* 288:121–132, 1999) LY274614 (Tiseo, P. J. and Inturrisi C. E., *J. Pharmacol. Exp. Ther.* 264:1090–1096, 1993); and NMDA antagonists that act on the glycine B site (Danysz, W. and C. G. Parsons, *Pharmacol. Rev.* 50:597–664, 1998).

Many different types of assays, with many variations of each type, have been used by those of skill in the art to test compounds for the properties of an NMDA receptor antagonist. Triton-treated membrane fractions prepared from rat telencephalon (including cortex, hippocampus, and striatum) can be used in binding assays to determine $K_D$'s of compounds; the effects of various compounds on [$^3$H] glycine binding can be determined, yielding a $K_i$, (Kessler, M. et al., *J. Neurochem* 52:1319–1328, 1989). Ebert, B. et al. (*Eur. J. Pharmacol. Mol. Pharmacol.* 208:49–52, 1991) have described assays that determine $K_i$ values of compounds by evaluating their affinities to membrane fractions isolated from various parts of the rat brain. It was found that the test compounds showed markedly lower affinity for the MK-801 binding sites in the rat cerebellum compared to MK-801 binding sites in the cortex (approximately 25-fold lower). $K_D$ values were similar for rat cortex, hippocampus, striatum, midbrain and medulla pons, although $B_{max}$ values (indicating density of binding sites) for these tissues varied considerably.

In other types of tests of compounds for properties of NMDA receptor antagonists, onset and relief of block of NMDA-induced voltage-clamped neuron currents can be measured after application of a compound (Mealing, G. A. R. et al., *J. Pharmacol. Exp. Ther.* 288:204–210 (1999); Mealing, G. A. R. et al., *J. Pharmacol. Exp. Ther.* 281:376–383 (1997)). Trapping of block by NMDA antagonists has been studied by a method described also in Mealing, G. A. R. et al., *J. Pharmacol. Exp. Ther.* 288:204–210 (1999) and in Blanpied, T. A. et al., *J. Neurophysiol.* 77:309–323 (1997), measuring current amplitudes on rat cortical neurons. Tests of the effectiveness of NMDA receptor antagonists as antinociceptive agents are the rat tail-flick test and the formalin test, both described in Shimoyama, N. et al., *J. Pharmacol. Exp. Ther.* 283:648–652 (1997). Other assays for NMDA receptor binding and effects of this binding are referred to in the review by Danysz and Parsons, *Pharmacological Reviews* 50(4):597–664, 1998.

Preferred NMDA receptor antagonists are those which have a $K_D$ in an NMDA receptor binding assay greater than 10 $\mu$M and less than or equal to 100 $\mu$M, more preferred are those NMDA receptor antagonists which have a $K_D$ greater than 1 $\mu$M and less than or equal to 10 $\mu$M, even more preferred are those NMDA receptor antagonists which have a $K_D$ greater than 100 nM and less than or equal to 1 $\mu$M, still more preferred are those NMDA receptor antagonists which have a $K_D$ greater than 10 nM and less than or equal to 100 nM, and most preferred are those NMDA receptor antagonists which have a $K_D$ equal to or less than 10 nM.

There is evidence for three major categories of opioid receptors in the central nervous system. These have been designated $\mu$, $\kappa$, and $\delta$. Binding to the opioid receptors can be measured in assays such as those described in Kristensen, K. et al., *Life Sciences* 55(2):PL45–PL50 (1994), using bovine caudate nucleus. Opioid receptor binders (which act either as an agonist or antagonist) are those compounds that bind to opioid receptors with a dissociation constant of less than about 100 nM. Preferably, opioid receptor binding molecules bind to opioid receptors with a $K_D$ of less than 10 nM. A given opioid drug may interact to a variable degree with all three types of receptors and act as an agonist, partial agonist, or antagonist, at each type of receptor. The antagonist naloxone binds with high but variable affinity to all of these receptors. The term "naloxone-sensitive" is sometimes used synonymously with "opioid" in describing the actions of a given compound. See Jaffe, J. H. and W. R. Martin, "Opioid Analgesics and Antagonists," pp. 485–521 In *The Pharmacological Basis of Therapeutics* (A. G. Gilman et al., eds.), 8th ed., Pergamon Press, New York, 1990.

Compounds classified as opioids have the ability to bind to opioid receptors. These can be natural or synthetic compounds. It has been found that some opioids tested for binding to the NMDA receptor are NMDA receptor antagonists (Ebert, B. et al, *Biochemical Pharamacology* 56:553–559, 1998). Within the class of compounds that are opioids and are NMDA receptor antagonists is a subset of compounds that can exist as (−) and (+) forms. Where the enantiomers have been tested for binding affinity to NMDA receptors, both have been found to have binding activity; for some of these compounds, the (+) enantiomer has been demonstrated as having a higher affinity for NMDA receptors (Gorman, A. L., et al., *Neurosci. Lett.* 223:5–8, 1997; Choi, D. W. and V. Viseskul, *Eur. J. Pharmacol.* 155:27–35, 1988; Craviso, G. L. and Musacchio, J. M., *Molec. Pharmacol. Exp. Ther.* 264:1090–1096, 1993).

While Applicants do not wish to be bound by a single mechanism of action of the methods of the claims, one hypothesis that explains the results observed in the Examples is that both narcotic agonists and narcotic antagonists can bind to NMDA receptors and act as antagonists of NMDA receptors. Support for this hypothesis can be found in the scientific literature: (1) narcotic agonists and antagonists bind to NMDA receptors (see study of inhibition of binding of [$^3$H]dextromethorphan in Craviso, G. L. and J. M. Musacchio, *Molec. Pharmacol.* 23:629–640, 1983); (2) both (+) and (−) enantiomers can bind to NMDA receptors, with the (+) enantiomer in most cases having a higher affinity for the NMDA receptor (see Craviso, G. L. and Musacchio, J. M. *Molec. Pharmacol.* 23:629–640, 1983); also see study of inhibition of binding of MK-801 to NMDA receptors in synaptic membranes from rat forebrain in Gorman, A. L. et al., *Neurosci. Lett.* 223:5–8, 1997); (3) like compounds previously characterized as NMDA antagonists, narcotic agonists and antagonists can protect cultured neurons from glutamate toxicity (Choi, D. W. and Viseskul, V. *Eur. J. Pharmacol.* 155:27–35, 1988).

Assuming that both (+) and (−) enantiomer of narcotic antagonists decrease stereotypic behaviors by blocking NMDA receptors, there are considerable advantages to be gained by employing (+) enantiomers. These are: (1) there is no induction of narcotic receptors; (2) narcotics can be employed for pain relief if necessary (e.g. oral surgery or other surgery), as (+) enantiomers of narcotic antagonists do not block narcotic analgesia. The (+) enantiomers, unlike some known NMDA antagonists, readily cross the blood brain barrier. They do not produce toxic side effects like dizocilpine (MK-801). There is much experience with dextromethrophan as an anti-tussive with very little toxicity. Furthermore, there is considerable experience in treating addiction with (−) naltrexone and with racemic methadone. Toxicity of these substances is minimal.

Substituting (+) methadone for racemic methadone or (−) acetyl-1 methadol in the treatment of narcotic addicts would have many advantages, including: 1) decreased craving without maintaining addiction; 2) no tolerance, and therefore lower doses; 3) no problems with security or drug diversion; and 4) less difficulty in weaning addicts. Block of NMDA receptors should also decrease craving for cocaine and alcohol (Sass, H. et al., *Arch. Gen. Psychiarty* 53:673–680, 1996; Mitchem, L. D. et al., *Pharmacol. Biochem. Behavior* 62:97–102, 1999).

Preferred compounds to be used in the treatment of repetitive behavior disorders include (+) enantiomers of both natural and synthetic opioids, such as dextromethorphan, dextrorphan, (+) methadone and (+) pentazocine; (+) enantiomers of synthetic narcotic antagonists such as (+) naloxone, (+) naltrexone, (+) nalmefene, and (+) diprenorphine.

Compositions to be used in methods described herein for the treatment of stereotypic, self-injurious and compulsive behaviors in animals and in humans include those comprising NMDA receptor antagonists; those compositions comprising NMDA receptor antagonists, wherein the composition does not comprise haloperidol; those compositions comprising NMDA receptor antagonists, wherein the composition does not comprise haloperidol, and wherein the composition does not comprise primarily (−) enantiomer of an opioid receptor agonist or antagonist; compositions comprising NMDA receptor antagonists, wherein the composition does not comprise haloperidol, and wherein the composition does not comprise an opioid receptor agonist or antagonist as (−) or (+) enantiomer; also, compositions comprising a compound selected from the group consisting of: dextromethorphan, dextrorphan, naltrexone, naloxone, methadone, pentazocine, nalmefene, diprenorphine, nalorphine, hydromorphone, oxymorphone, hydrocodone, oxycodone, buprenorphine, butorphanol, nalbuphine, fentanyl, metazocine, cyclazocine, etazocine, and a combination of any of the preceding, wherein the compounds are predominantly (+) enantiomer.

Further compounds which can be used, preferably topically, in a composition for the treatment of behaviors such as psychogenic excoriation and scratching associated with pruritus are compounds such as loperamide, MK-801, and ketamine, wherein the compound is primarily (+) enantiomer, of those that are optically active.

Animals to be treated for repetitive behaviors include, but are not limited to, birds and mammals, for example, captive "wild" birds and mammals, such as those living in zoos or animal preserves, especially species that are predatory or can be predatory, such as feline, canine and ursine species, domestic animals, such as those raised for meat or furs (e.g., chickens, pigs, cattle, minks), and those animals kept as pets or for recreational purposes, such as rats, mice, cats, dogs, horses, and various types of birds, such as parrots, cockatoos, parakeets, pigeons and the like.

"Horses" as used herein includes those domesticated animals that are usually called "horses," but also those animals that are sometimes classified by size as being ponies or miniature horses.

"Of an equine species" refers herein not only to horses, donkeys, and the like but also to equine hybrids, such as mules and hinnies.

Similarly, "of a canine species" refers herein not only to domestic dogs, but also to wild dogs and canine hybrids.

Stereotypic movement disorder of humans is characterized by "repetitive, seemingly driven, and nonfunctional motor behavior (e.g., hand shaking or weaving, body rocking, head banging, mouthing of objects, self-biting, picking at skin or bodily orifices, hitting own body)." The severity of the behavior is such that it interferes with normal activities or results in bodily injury if preventive measures were not used. Self-injuries behaviors occur in certain medical conditions associated with mental retardation (e.g., fragile X syndrome, de Lange syndrome, and Lesch-Nyhan syndrome, characterized by self-biting). See pages 118–121 In *Diagnostic and Statistical Manual of Menial Disorders* (DSM-IV™), American Psychiatric Association, 1994.

Smoking compulsion in humans is the urge to perform the act of smoking (tobacco cigarettes, cigars, or tobacco contained in another vessel or vehicle). The act of smoking is the physical manipulation of the cigarette or other tobacco vehicle and the conscious control of breathing that is normally performed in the course of taking in and blowing out the tobacco smoke, primarily involving the hands and mouth, in a kind of ritual. Smoking compulsion usually accompanies the well-documented nicotine addiction resulting from frequent and habitual tobacco smoking, but can be thought of as a compulsion which is separate from the craving satisfied by the administration of nicotine by a route other than smoking. This compulsion to smoke may be responsible for the failure of the simple administration of decreasing doses of nicotine (by transdermal patch or by nicotine-containing chewing gum, for example) to wean smokers from their smoking habit.

Psychogenic excoriation (also sometimes referred to as neurotic excoriation or pathologic skin picking) is a human disorder characterized by excessive scratching, picking, gouging, or squeezing the skin, and occurs in approximately 2% of dermatology clinic patients, mostly female (Gupta, M. A. et al., *Compr. Psychiatry* 27:381–386, 1986). It has been hypothesized that psychogenic excoriation is an impulse control disorder which is related to obsessive-compulsive disorder, or which is a manifestation of obsessive-compulsive disorder (McElroy, S. L. et al.,*J. Clin. Psychiatry* 55:33–53, 1994). Patients with psychogenic excoriation have responded to serotonin reuptake inhibitors such as fluoxetine and sertraline (Gupta, M. A. and A. K. Gupta, *Cutis* 51:386–387, 1993; Stein, D. J. et al., *Psychosomatics* 34:177–181, 1993; Phillips, K. A. and S. L. Taub, *Psychopharmacol. Bull.* 31:279–288, 1993; Kalivas, J. et al., *Arch. Dermatol* 132:589–590, 1996). In a study of fluvoxamine (a selective serotonin reuptake inhibitor used in the treatment of OCD) for the treatment of psychogenic excoriation, patients showed significant improvement (Arnold, L. M. et al., *Journal of Clinical Psychopharmacology* 19:15–18, 1999).

In what can also be considered a related self-injurious behavior, scratching associated with pruritus has been shown to respond to peripherally acting opiates, such as loperamide (U.S. Pat. Nos. 5,849,761; 5,849,762). An animal model, using injections of a chemical irritant, can be used to test the effectiveness of agents to treat scratching associated with pruritis (Kuraishi, Y. et al., *European Journal of Pharmacology* 275: 229–233, 1995).

An effective amount of an agent, a compound or a drug is an amount that produces a measurable improvement in the condition to be treated (e.g., a reduction in the frequency of the behavior exhibited in the human or animal, compared to the frequency of behaviors exhibited in a human or animal left untreated or sham-treated).

A compound primarily in the (+) form can be from greater than 50% to 100% (+) enantiomer. Similarly, a compound that is primarily (−) can be from greater than 50% (in a racemic mixture) to 100% (−) enantiomer. Compositions comprising primarily the (+) form of an opioid can have greater than 50% to 60% (+) enantiomer, but preferably have greater than 60% to 70% (+) enantiomer, more preferably greater than 70% to 80% (+) enantiomer, still more preferably greater than 80% to 90% (+) enantiomer, and most preferably, more than 90% (+) enantiomer.

Agents to be used in methods of treating a human or an animal for a repetitive and/or compulsive behavior disorder can be employed in combination with a non-sterile or sterile carrier or carriers for use with cells, tissues or organisms, such as a pharmaceutical carrier suitable for administration to a human or animal subject. Such compositions comprise, for instance, a media additive or a therapeutically effective amount of an agent and a pharmaceutically acceptable carrier or excipient. Such carriers may include, but are not limited to, saline, buffered saline, dextrose, water, ethanol, surfactants, such as glycerol, excipients such as lactose and combinations thereof. The formulation can be chosen by one of ordinary skill in the art to suit the mode of administration. The chosen route of administration will be influenced by such factors as the solubility, stability and half-life of the agent, for instance. Agents to be used in the treatment of a repetitive and/or compulsive behavior disorder may be employed alone or in conjunction with other compounds, such as other therapeutic compounds. The pharmaceutical compositions may be administered in any effective, convenient manner, including administration by topical, oral, anal, vaginal, intravenous, intraperitoneal, intramuscular, subcutaneous, intranasal, transdermal or intradermal routes, among others. In therapy or as a prophylactic, the active agent may be administered to a subject as an injectable composition, for example as a sterile aqueous dispersion, preferably isotonic, or "packaged" as liposomes or microspheres.

When injectable compositions are desired, the functional antagonists of the present invention may be formulated, for example, into preparations for injection by dissolving, suspending or emulsifying them in an aqueous or non-aqueous solvent, such as vegetable oil, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Alternatively, if one wishes to prepare an oral dosage form containing one of the functional antagonists herein encompassed, commonly used and pharmaceutically acceptable tableting excipients, such as lactose, microcrystalline cellulose, corn starch, stearic acid, or the like, may be used, if desired, to prepare such dosage forms.

Alternatively, the composition may be formulated for topical application, for example, in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions.

In addition, the amount of the compound will vary depending on the size, age, body weight, general health, sex, and diet of the host, and the time of administration, the biological half-life of the compound, and the particular characteristics and symptoms of the disorder to be treated. Adjustment and manipulation of established dose ranges are well within the ability of those of skill in the art, and preferably minimize side effects and toxicity.

EXEMPLIFICATION

EXAMPLE 1
Treatment of Cribbing in Horses

Horses were admitted to the Large Animal Hospital of Tufts University School of Veterinary Medicine or were tested in their home barn. Cribbing straps and food were removed prior to testing. Control rates of crib-biting were observed and recorded for 5 minute intervals for one hour or more after an intravenous injection of 0.15 M saline. Test drugs were administered orally (by gavage) or by injection into the jugular vein. Solutions were made up with physiological saline and sterilized by filtration through a 0.2 micron filter (Millipore).

For the experimental data shown in FIG. 1, after establishment of a stable control rate of approximately 10 crib-bites per minute, 50 mg of D-methadone-HCl in 25 ml saline was injected i.v. In FIG. 1, the cumulative number of crib-bites was plotted against time as was the rate per 5 minute interval (Shuster, L. and N. H. Dodman, pp. 185–202, In *Psychopharmacology of Animal Behavior Disorders*, (N. H. Dodman and L. Shuster, eds.), Blackwell Scientific, Malden, Mass., 1998). The rate decreased between the second and the fifth 5-minute interval following injection. The control rate then resumed during the next 80 minutes of observation. Horses were observed continuously during scoring for side effects that might be attributed to the treatment. These included changes in posture, disposition and motor activity. See also Table 1.

EXAMPLE 2
Treatment of Stall-walking in Horses

Figure 2:
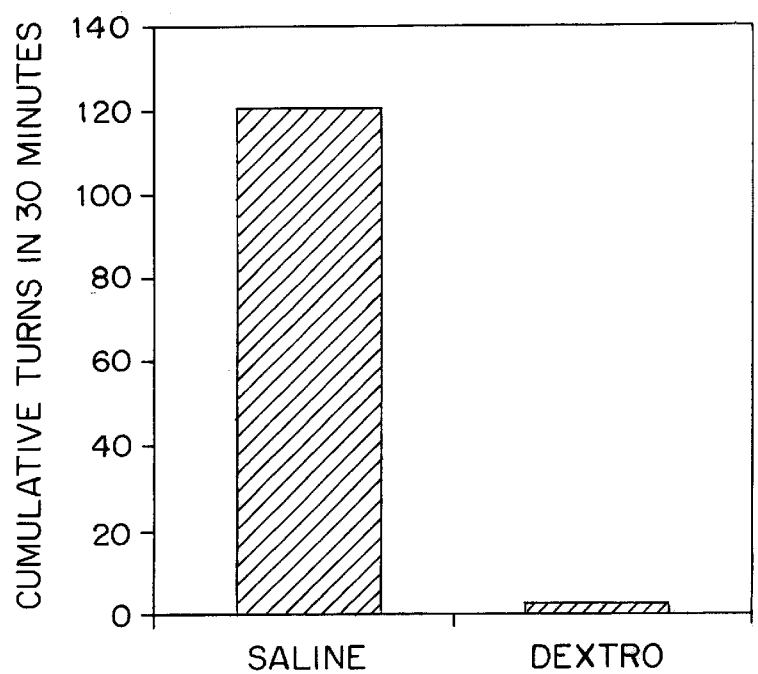
FIG. 2 is a bar graph in which the cumulative number of turns of the stall in 30 minutes are plotted for a stall-walking horse observed before and after the injection of dextromethorphan. Dextromethorphan-HBr, 1.0 mg/kg i.v., was injected after 60 minutes of control observations. "Saline" indicates the number of turns by the horse, observed in 30 minutes after injection of saline. "Dextro" indicates the number of turns by the horse, observed in 30 minutes after injection of dextromethorphan.

Dextromethorphan-HBr, 1.0 mg/kg i.v., was injected after 60 minutes of control observations, to test its effect on a stall-walking horse. When measuring "stall walking" locomotor activity, each circuit around the stall was scored as one rotation. Cumulative rotations per 5 minute interval were plotted against time to establish the rate of circling. The results of the experiment are plotted in FIG. 2. See also Table 1.

TABLE 1

Effect of some Drug Treatments on the Rate of Crib Biting

| Horse | Drug Dose & Route | Duration of Effect | Crib-biting Frequency number per minute Before treatment | Number per minute After treatment |
| --- | --- | --- | --- | --- |
| CB | (−) naloxone .04 mg/kg, i.v. | 65 min. (10 min lag) | 12 | 0.1 |
| CB | (+) naloxone 0.12 mg/kg, i.v. | 60 min. (30 min lag) | 10 | 6.6 |
| CB | (+) naloxone 0.18 mg/kg, i.v. | 60 min. (no lag) | 9.2 | 0.8 |
| CB | Dextromethorphan 1.0 mg/kg, p.o. | 90 min. (35 min lag) | 8 | 1.7 |
| CB | Dextromethorphan 1.0 mg/kg, i.v. | 35 min (no lag) | 7.6 | 0.3 |
| CB | (+) Methadone 0.2 mg/kg, i.v. | 20 min (10 min lag) | 8.8 | 2.6 |
| CB | (+) Methadone .01 mg/kg, i.v. | 10 min | 8.2 | 5.5 |
| CB | ketamine 0.2 mg/kg, i.v. | 50 min (no lag) | 8.2 | 1.3 |
| Frito | Dextromethorphan 3.2 mg/kg p.o. | 100 min (30 min lag) | 3.5 | |
| Full Circle (turning) | Dextromethorphan 1.0 mg/kg,. i.v. | 45 min (no lag) | 3.5 turns per min. | .3 turns per min. |

EXAMPLE 3
Treatment of Light/shadow-chasing in Dogs

Figure 3:
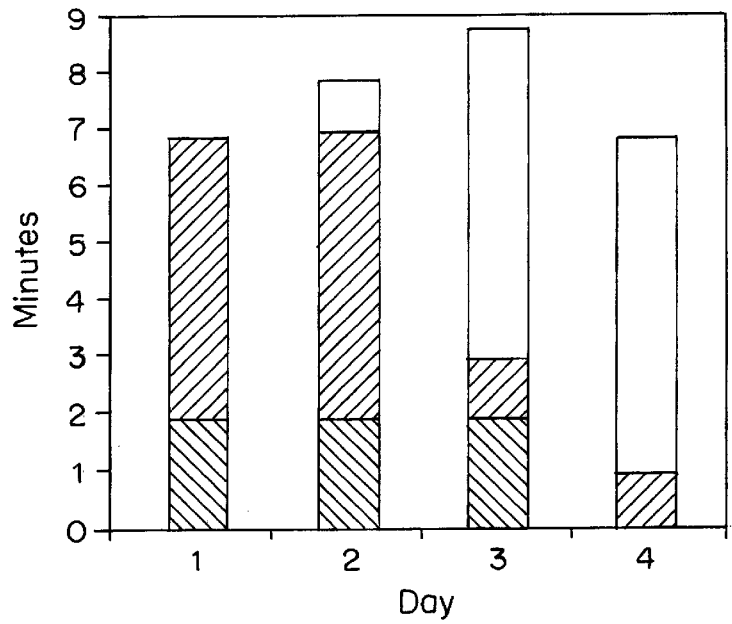
FIG. 3 is a bar graph showing the time spent in three typical behaviors in four experiments in which the effect of dextromethorphan on a shadow-chasing dog was tested on four consecutive days. back slash hatching indicates "searching"; forward slash hatching indicates "fixated"; white indicates "resting." Dextromethorphan-HBr, 2 mg per kg p.o. was administered twice daily, and testing was carried out one hour after the morning dose. Bars indicate the total time of each of three behaviors during the first 10 minutes after the beginning of testing. Time not accounted for was spent in moving about the room, usually out of range of the camera.

Behavior of a shadow-chasing dog was filmed with a video camera for 10 minutes after the onset of testing in the owner's home. To stimulate the dog, the owner moved around a flashlight beam on the floor for 5 seconds. The typical response after the light was turned off was frantic searching for the light followed by fixed staring at the floor. Dextromethorphan-HBr, 2 mg per kg p.o. was administered twice daily and testing was carried out one hour after the morning dose. Results are shown in FIG. 3.

EXAMPLE 4
Mouse Model for Pruritus

Figure 4:
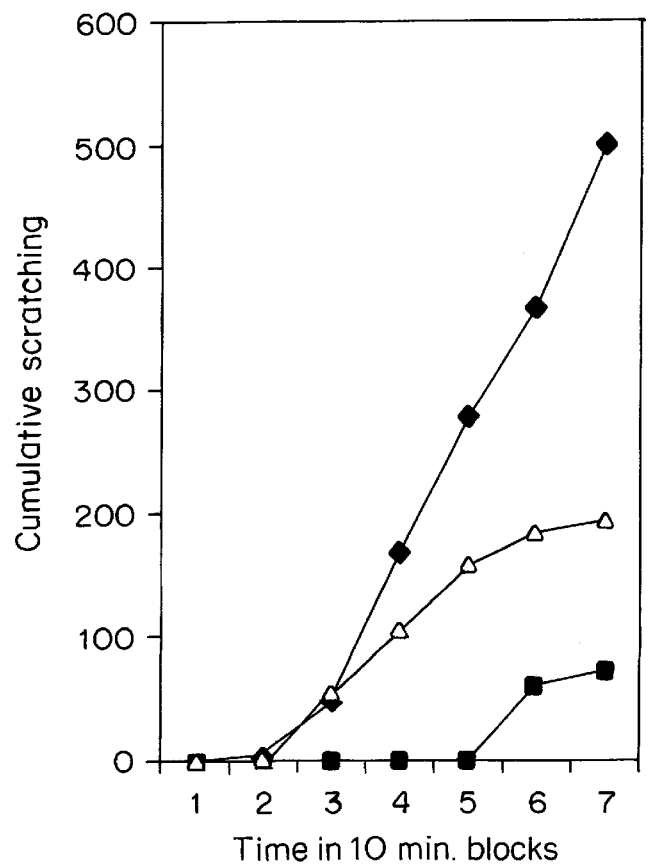
FIG. 4 is a graph of the cumulative number of scratches by a mouse, plotted at 10 minute intervals, when naltrexone (10 mg/kg; squares), dextromethorphan (10 mg/kg; triangles), or no compound (control; diamonds) was injected into the mouse 10 minutes before injection of compound 40/80.
Figure 5A:
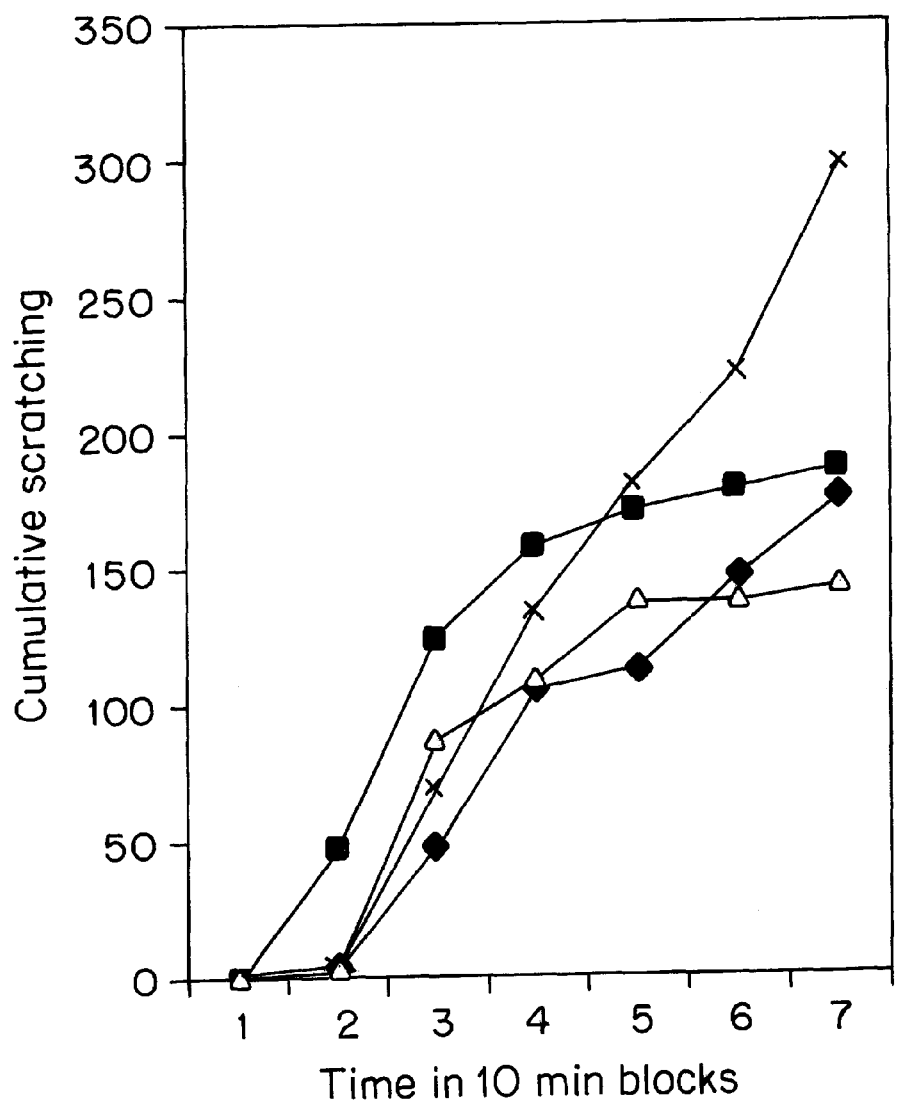
FIG. 5A is a graph of the cumulative number of scratches by a mouse, plotted at 10 minute intervals, when haloperidol (2.0 mg/kg; triangles), dextromethorphan (20 mg/kg; squares), (+) naloxone (20 mg/kg; diamonds), or saline (control; X's) was injected into the mouse 30 minutes after injection of compound 40/80.
Figure 5B:
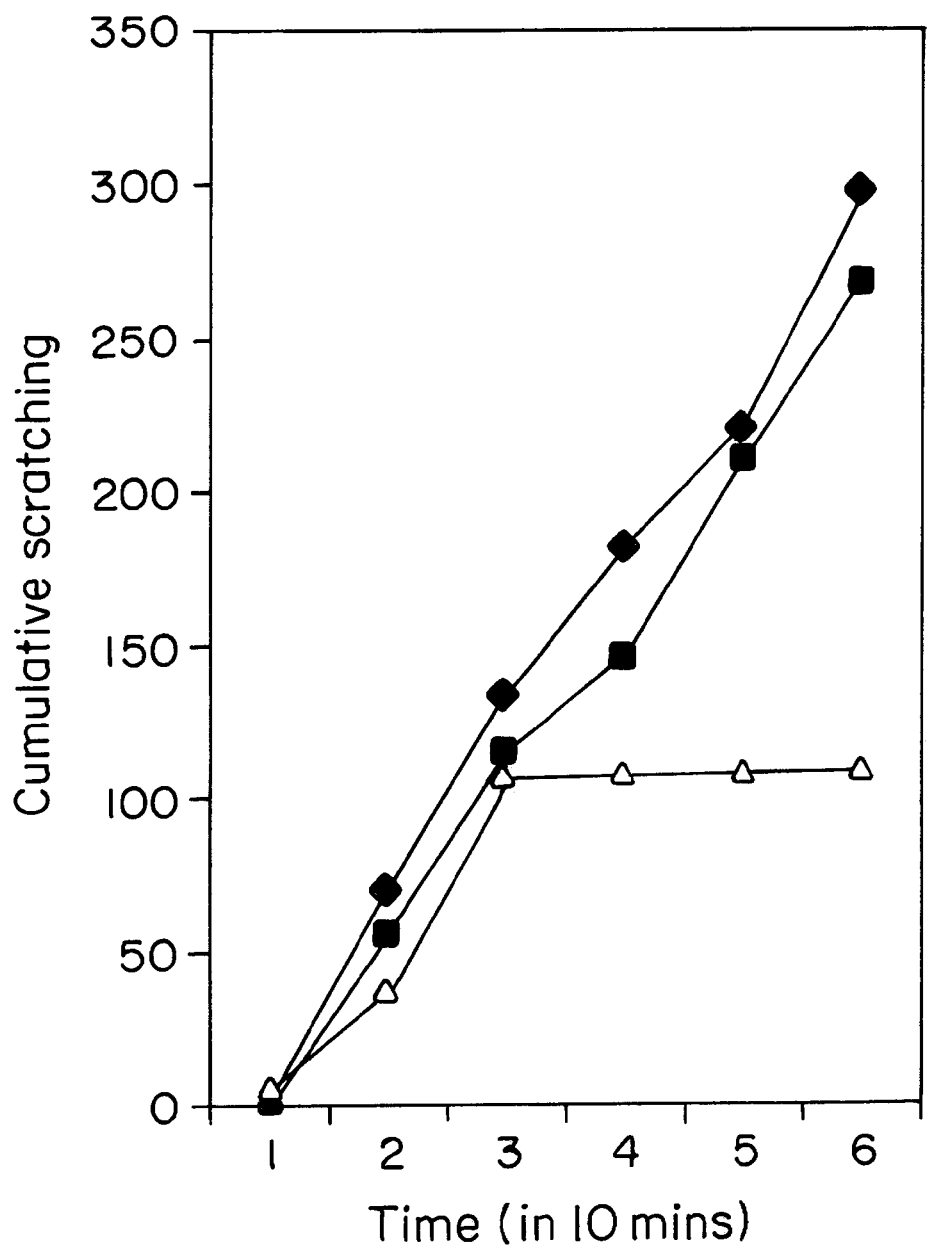
FIG. 5B is a graph of the cumulative number of scratches by a mouse, plotted at 10 minute intervals, when (+) methadone (5.0 mg/kg; squares), (+) methadone (10 mg/kg; triangles), or saline (control; diamonds) was injected into the mouse 30 minutes after injection of compound 40/80.

The animals used were BALB/c male mice, weighing 27–33 g. One mouse was used per compound tested, except for two control mice receiving saline; two different mice were tested with (+) methadone, each with a different dose. Compound 48/80 (Kuraishi, Y. et al., *European Journal of Pharmacology* 275:229–233, 1995), 0.5 mg/ml in saline, was injected subcutaneously in a volume of 0.1 ml, between the shoulder blades of the mouse. Test treatment compounds, dissolved in saline, were injected intraperitoneally in a volume of 0.1 ml per 10 g, either 10 minutes before or 30 minutes after injection of compound 48/80. The cumulative number of scratches with a hind leg were recorded at 10 minute intervals for 60 minutes following the injection of compound 48/80. See Tables 2 and 3, as well as FIGS. 4, 5A and 5B, showing the effectiveness of the compounds tested: naltrexone, dextromethorphan, (+) methadone, haloperidol, and (+) naloxone.

TABLE 2

Effect of NMDA Blockers on Pruritus in Mouse: Blocker Administered 10 Minutes Before 48/80

| | Cumulative Scratches | | |
|---|---|---|---|
| Time Minutes | Control | Naltrexone 10 mg/kg | Dextromethorphan 10 mg/kg |
| 10 | 5 | 0 | 1 |
| 20 | 52 | 0 | 57 |
| 30 | 166 | 0 | 105 |
| 40 | 277 | 1 | 157 |
| 50 | 364 | 61 | 182 |
| 60 | 498 | 73 | 192 |

| Time | (+) methadone 10 mg/kg | Control |
|---|---|---|
| 10 | 0 | 3 |
| 20 | 0 | 79 |
| 30 | 0 | 99 |
| 40 | 0 | 227 |
| 50 | 0 | 404 |
| 60 | 0 | 456 |

TABLE 3

Effect of NMDA Blockers on Pruritus in Mouse: Compound Administered 30 Minutes After 48/80

| | | Cumulative Scratches | | | |
|---|---|---|---|---|---|
| Time | Saline | (+) Meth-adone 5 mg/kg | (+) Meth-adone 10 mg/kg | (+) Naloxone 20 mg/kg | Dextro-methor-phan 20 mg/kg | Halo-peridol 2.0 mg/kg |
| 10 | 4 | 0 | 6 | 4 | 47 | 2 |
| 20 | 70 | 56 | 38 | 48 | 125 | 87 |
| 30 | 134 | 114 | 106 | 105 | 158 | 108 |
| 40 | 181 | 145 | 107 | 112 | 171 | 137 |
| 50 | 220 | 210 | 107 | 146 | 178 | 137 |
| 60 | 297 | 267 | 107 | 175 | 185 | 142 |

All references cited herein not previously specifically stated as being incorporated by reference are hereby incorporated by reference in their entirety.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method for treating a repetitive behavior disorder in an animal, comprising administering to the animal an effective amount of a composition comprising one or more NMDA receptor antagonists, wherein the composition does not comprise haloperidol, and wherein the composition does not comprise all (−) enantiomer or primarily (−) enantiomer of an opioid receptor agonist or antagonist.

2. A method for treating a repetitive behavior disorder in a horse, comprising administering to the horse an effective amount of a composition comprising one or more NMDA receptor antagonists, wherein the composition does not comprise haloperidol and does not comprise primarily (−) enantiomer of an opioid receptor agonist or antagonist.

3. A method for treating a repetitive behavior disorder in a horse, comprising administering to the horse an effective amount of a composition comprising one or more NMDA receptor antagonists, wherein the composition does not comprise haloperidol and does not comprise primarily (−) enantiomer of an opioid receptor agonist or antagonist, and wherein the repetitive behavior disorder is selected from the group consisting of: cribbing, wind sucking, stall walking, weaving, head bobbing, pawing, tonguing, self-biting, and head shaking.

4. A method for treating a repetitive behavior disorder in an animal, comprising administering to the animal an effective amount of a composition comprising a compound selected from the group consisting of: dextromethorphan, dextrorphan, naltrexone, naloxone, methadone, pentazocine, nalmefene, diprenorphine, nalorphine, hydromorphone, oxymorphone, hydrocodone, oxycodone, buprenorphine, butorphanol, nalbuphine, fentanyl, metazocine, cyclazocine, etazocine, and a combination of any of the preceding, wherein the compounds are predominantly (+) enantiomer.

5. The method of claim 1 wherein the animal is a dog.

6. The method of claim 1 where the animal is a canine species.

7. A method for treating crib biting in an animal of an equine species, comprising administering to the animal an effective amount of a composition comprising one or more NMDA receptor antagonists, wherein the composition does not comprise primarily (−) enantiomer of an opioid receptor agonist or antagonist.

8. A method for treating crib biting in an animal of an equine species, comprising administering to the animal an effective amount of a composition comprising one or more NMDA receptor antagonists, wherein the composition does not comprise haloperidol, and wherein the composition does not comprise an opioid receptor agonist or antagonist as (−) or (+) enantiomer.

9. A method for treating crib biting in an animal of an equine species, comprising administering to the animal an effective amount of a composition comprising a compound selected from the group consisting of: (+) methadone, dextromethrophan, (+) naloxone, ketamine, and a combination of any of the foregoing compounds.

10. A method for treating stall walking in an animal of an equine species, comprising administering to the animal an effective amount of a composition comprising one or more NMDA receptor antagonists, wherein the composition does not comprise primarily (−) enantiomer of an opioid receptor agonist or antagonist.

11. A method for treating stall walking in an animal of an equine species, comprising administering to the animal an effective amount of a composition comprising one or more NMDA receptor antagonists, wherein the NMDA receptor antagonist is not an opioid receptor agonist or antagonist, and is not haloperidol.

12. A method for treating a repetitive behavior disorder in an animal of an equine species, comprising administering to the animal an effective amount of a composition comprising dextromethorphan.

* * * * *